United States Patent [19]

Cohn

[11] Patent Number: 5,422,495

[45] Date of Patent: Jun. 6, 1995

[54] OPTICAL SENSOR HAVING A FLOATATION MEANS FOR DETECTING FLUIDS THROUGH REFRACTIVE INDEX MEASUREMENT

[75] Inventor: Ralph F. Cohn, Waltham, Mass.

[73] Assignee: Boston Advanced Technologies, Inc., Newton, Mass.

[21] Appl. No.: 47,809

[22] Filed: Apr. 15, 1993

[51] Int. Cl.$^6$ .............................................. G01N 15/06
[52] U.S. Cl. .............................. 250/573; 250/227.14; 73/293
[58] Field of Search .................... 250/573, 577, 227.14, 250/901–908; 356/133; 73/293, 305, 307, 309

[56] References Cited

U.S. PATENT DOCUMENTS

| | | |
|---|---|---|
| 3,311,014 | 3/1967 | Witt et al. ............................ 356/133 |
| 3,448,616 | 6/1969 | Wostl et al. . |
| 4,038,650 | 7/1977 | Evans et al. . |
| 4,039,845 | 8/1977 | Oberhansli et al. . |
| 4,082,959 | 4/1978 | Nakashima . |
| 4,159,420 | 6/1979 | Tsunoda . |
| 4,311,048 | 1/1982 | Merz . |
| 4,353,252 | 10/1982 | Jeans . |
| 4,443,699 | 4/1984 | Keller .................................. 250/904 |
| 4,489,602 | 12/1984 | Henning . |
| 4,710,353 | 12/1987 | Tanaka et al. . |
| 4,711,126 | 12/1987 | Houpt et al. ........................ 356/133 |
| 4,745,293 | 5/1988 | Christensen . |
| 4,880,971 | 11/1989 | Danisch . |
| 4,942,306 | 7/1990 | Colbourne . |
| 4,998,022 | 3/1991 | Tregay . |
| 5,164,608 | 11/1992 | Vali et al. . |

FOREIGN PATENT DOCUMENTS

| | | |
|---|---|---|
| 1061476 | 6/1976 | Canada . |
| 0229960 | 12/1986 | European Pat. Off. . |
| 0334533 | 12/1986 | European Pat. Off. . |
| 0347095 | 6/1989 | European Pat. Off. . |
| 0450256 | 12/1990 | European Pat. Off. . |
| 0453226 | 4/1991 | European Pat. Off. . |

OTHER PUBLICATIONS

Publication–(2 pages), for IMO Industries, Inc., entitled "Compact, Low Cost, Plastic, Electro-Optic Liquid Level Switches", Jan. 1993.

Article (pp. 47–50, 52–53) in Sensors, Sep. 1992, entitled "Sensors in Flexible-Fuel Vehicles" by Bill Siuru.

Article–(12 pages), entitled "Removing Index of Refraction Contraints in the Optical Measurements of Liquid Level" by Lee A. Danisch, Jan. 1993.

Primary Examiner—David C. Nelms
Assistant Examiner—Que T. Le
Attorney, Agent, or Firm—Thomas J. Engellenner; Carolyn G. d'Agincourt; Lahive & Cockfield

[57] ABSTRACT

The present invention provides methods and systems for sensing the presence of fluids, such as hydrocarbon-based liquids and/or water, in an ambient environment based upon their light refractive properties. An optical waveguide is deployed in the environment (or a sample chamber disposed within the environment), such that the transmittance of light through the waveguide is attenuated in the presence of the fluid analyte. In one preferred embodiment, the light source is aligned with the waveguide, such that the light entering the waveguide enters one end at an angle relative to the central axis of the waveguide and propagates by internal reflection within the waveguide. Optimal propagation occurs in the absence of the fluid while the presence to the fluid in contact with the waveguide walls causes detectable losses in light propagation due to degradation of the internal reflectance.

36 Claims, 7 Drawing Sheets

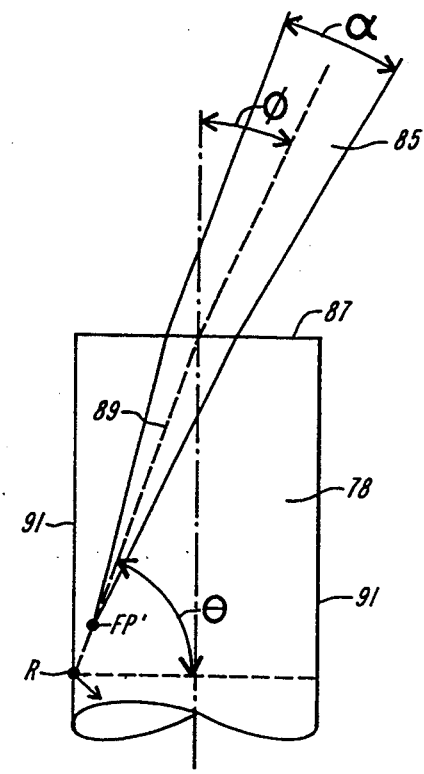 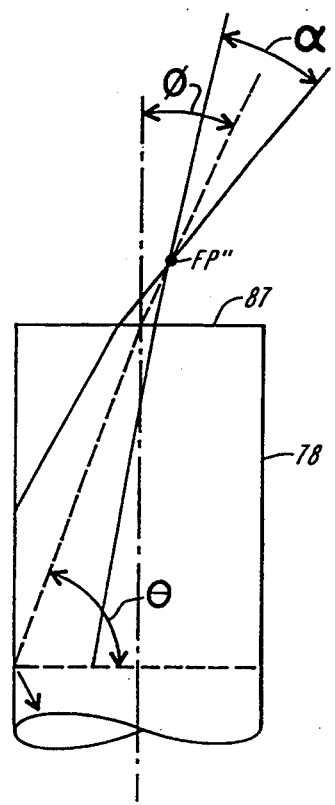
*FIG. 8A*  *FIG. 8B*
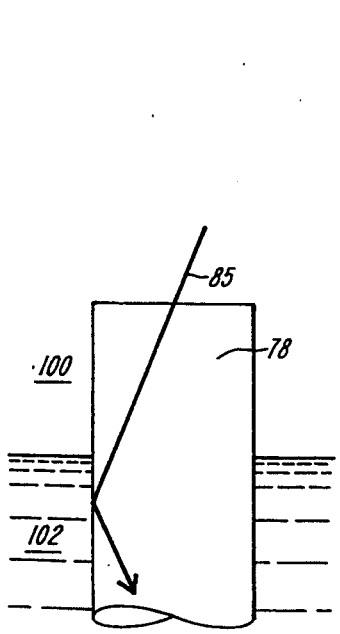 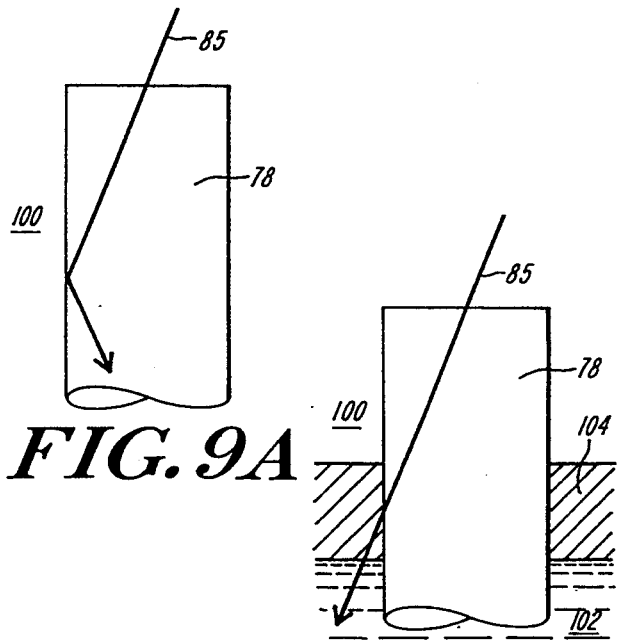
*FIG. 9B*  *FIG. 9A*  *FIG. 9C*

OPTICAL SENSOR HAVING A FLOATATION MEANS FOR DETECTING FLUIDS THROUGH REFRACTIVE INDEX MEASUREMENT

BACKGROUND OF THE INVENTION

The technical field of this invention concerns methods and apparatus for optically detecting the presence of fluids and, in particular, sensors for detecting undesirable fluids, such as hydrocarbons, if present in an ambient environment.

The detection and measurement of hydrocarbon fluid leaks and ground water contaminants, generally, is of considerable present interest. It is of particular interest to monitor the integrity of tanks containing potential environmental pollutants. For example, gasoline and oil tanks can cause severe contamination of the local environment, if such tanks or associated pipelines begin to leak. Moreover, when a dispenser of such fuels, such as typically found in a gasoline service station, is leaking, there is potential not only for environmental harm but also fires, explosions or other safety hazards.

Since it is usually impracticable to conduct manual or visual inspections of buried storage tanks and the inner pans or sumps of dispensing equipment, various sensor systems have been devised. For underground gasoline storage tanks, bore holes are typically drilled into the ground at various locations around the perimeter of the tank and physical ground water samples taken for off-site chemical analysis. However, such sampling is time-consuming and expensive. Moreover, because physically sampling is only a periodic action, it is unlikely to detect a leak or spill until significant damage has occurred.

Various instruments have also been proposed for non-physical and, in some instances, continuous monitoring of ground water and the like based on measurements, for example, of changes in dielectric properties of a sample or attenuation of light through a hydrocarbon-absorbing medium. Other systems have attempted to detect hydrocarbons by illuminating the sampling environment with light and measuring the fluorescence typically associated with hydrocarbons. However, these systems are typically expensive, sometimes inaccurate and often prone to maintenance problems.

It is an object of the present invention to provide improved, non-physical sensors and methods capable of either periodic or continuous monitoring of ground water, industrial facilities and commercial service stations for the presence of undesirable fluids in the environment.

It is another object of the present invention to provide an inexpensive, robust and compact sensor which can be placed, for example, in gasoline service station dispensor pans or sumps, or at other locations proximal to fuel tanks and other storage depots for hydrocarbon fuels or associated pipelines.

SUMMARY OF THE INVENTION

The present invention provides methods and sensors for sensing the presence of fluids, such as hydrocarbon-based liquids and/or water, in an ambient environment based upon their light refractive properties. Broadly, an optical waveguide is deployed in the environment (or a sample chamber disposed within the environment), such that the transmittance of light through the waveguide is attenuated in the presence of the fluid analyte.

The term "light" is used herein in the broad sense of electromagnetic radiation, which may be visible, or outside the visible spectrum (e.g., ultraviolet or infrared radiation) so long as the radiation is capable of transmission via the waveguide. The term "waveguide" is used herein to encompass any transmission medium within which light can be transmitted. Examples of waveguides include optical fibers, light pipes, and fuzed silica structures, as well as other glass or ceramic structures having suitable light transmission characteristics.

In one aspect of the invention, an optical waveguide is constructed having an optical axis along which light can be transmitted. The waveguide is disposed within the environment to be monitored in conjunction with a light source for projecting light into one end to the waveguide and a detector disposed at the other end to measure losses in the light passing through the waveguide. In one preferred embodiment, the light source is aligned with the waveguide, such that the light entering the waveguide enters the first end at an angle relative to the central axis of the waveguide and propagates by internal reflection within the waveguide. Optimal propagation occurs in the absence of the fluid while the presence to the fluid in contact with the waveguide walls causes detectable losses in light propagation due to degradation of the internal reflectance.

The invention is particularly useful in discriminating gasoline from air or water based on refractive index differences. In one embodiment, a sensing device is constructed within a columnar housing which permits it to freely travel vertically, allowing it to float on a water layer covering a wide range of possible depths. The device can detect the presence of water either optically or through the use of one or more proximity sensors disposed to determine when it has floated off the bottom and if it has reached the top of the columnar housing. A gasoline layer can be reliably detected even when floating on the surface of water within housing.

The detection principles of the present invention are based upon the measurement of the amount of light lost from a waveguide when in contact with a surrounding medium. The sensors of the present invention can be adjusted so that gasoline layers with thicknesses greater than a specified threshold level can trigger a shut-off switch, a display or an alarm. Thresholds can further be set so as to discriminate between trace amounts of gasoline, which may be present in the fuel distribution environment, and gasoline leaks which require attention, servicing or automatic shut-down protocols. The devices of the present invention may also be use to detect the presence of water.

The sensors use the property of total internal reflection which occurs when light passes from a higher to a lower refractive index medium at an appropriate angle of incidence. The angle at which total internal reflection occurs moves to progressively higher values with increases in the refractive index of the surrounding medium.

For gasoline detection, one chooses an angle at which total internal reflection occurs whenever air or water are present and transmission occurs when gasoline is introduced. Typically in glass or silica waveguides, air yields an angle of total internal reflection at approximately 44°, water at about 67°, and low index gasoline (the most difficult gasoline case to discriminate) at about 81°. Thus, selecting an internal reflection angle between about 67° and about 81° permits successful detection of gasoline while remaining insensitive to air or water.

Similarly, to detect the presence of water, the selection of an internal reflection angle between about 44° and about 67° is indicated. Sensors can also be constructed using alternating measurements at two angles to detect both water and gasoline.

Moreover, when a large vertical range is covered by the waveguide, a layer of gasoline floating on water can be successfully detected. The sensors can further be designed to discriminate between a trace amounts of gasoline (or "sheens") on the top of a water column, on one hand, and more extensive leaks requiring immediate remedial action (e.g., automatic shut-off of dispensers, warning display and/or alarm signals).

The internal reflectance angles discussed in this section represent the angles at the glass/fluid interface within the waveguide. While these angles are relevant to the transmission characteristics of the waveguide and critical to device's ability to sensor particular fluids in contact with the waveguide, the reflectance angle is most easily controlled by aligning the light source with the waveguide, such that a desired angle of incidence is obtained when the light enters the waveguide.

The angle of incidence and the reflectance angle will be roughly complementary, subject to the refraction of the light as it passes through the end face of the waveguide. (The light beam entering the waveguide is bent inward, i.e., towards the optical axis of the waveguide, to a degree dependent on the waveguide materials and the wavelength of light chosen). The relationship between the angle of incidence and the reflectance angle is well known and easily calculated.

For example, in a waveguide having an index of refraction of about 1.457, to achieve an internal reflectance angle at the glass/medium interface of about 72°, an angle of incidence of about 26.6° must be applied at the rod's end. Generally, it has been found that an angle of incidence ranging from about 24° to about 34°, more preferably from about 27° to about 31°, is typically useful in detecting gasoline with sensing devices according to the present invention.

Similarly, it has been found that an angle of incidence ranging from about 38° to about 75°, more preferably, from about 45° to about 65° is typically useful in detecting water.

In one preferred embodiment, the waveguide is a light pipe made from an optically transparent material whose optical refractive index is selected to be roughly centered within the range of index values exhibited by gasoline, which ranges from 1.43 to 1.47. For example, the waveguide can be formed from fused silica with a refractive index of 1.454.

The dimensions of the waveguide can be varied depending upon the application. The waveguide may be of any width, although the width will affect the sensitivity along the vertical dimension. In one preferred embodiment a cylindrical rod having a diameter ranging from about 0.5 to about 2.0 millimeters, more preferably about 1.0 mm can be employed. The rod is currently mounted at two points (top and bottom) by gluing it into holes in an optical mounting bracket.

To minimize light loss at the rod mounting points a layer of metallization is applied to act as a mirror. This greatly reduces the sensitivity of the output signal to variations in the angle or size of the beam from the optical source. Both ends of the rod are polished to an optical smoothness level to provide efficient light coupling.

The optical source should be selected so that a wavelength consistent with the previously specified refractive index range of the sensor rod is obtained. In one embodiment, a diode laser is used with an optical power level of 3 mW and a nominal wavelength of 780 nm (although non-laser light sources can also be employed). The sensor will function with the beam introduced at a wide range of angles of incidence at the top end of the waveguide (rod) ranging from vertical incidence to nearly 45°.

The optimum performance has been obtained with a focused beam having a focal point within the waveguide (either before or after an initial internal reflection). For example the incident light beam can have an angle of incidence of about 29° with approximately a 5° spread angle within the beam.

The optical source preferably maintains a constant optical power output over a wide range of temperatures. In many commercially available laser diode or LED packages, a photodiode internal to the package is used to stabilize the optical power. To minimize power consumption and heating of the laser, the source can be pulsed on for 5 to 500 ms every 1 to 5 seconds during which time a measurement is made.

A lens can be included in the laser diode housing to focus the optical beam. The lens can be adjusted to provide the desired optical spot size at the rod end. This spot size can effect the sensitivity of the device to thermal variations. A spot which fills a major portion of the end of the rod is currently preferred. In one embodiment, a threaded lens housing can be used to provide easy adjustment of the focus. Alternative arrangements are possible.

The material the laser/lens housing should provide adequate heat sinking for the laser and remain sufficiently dimensionally stable over temperature to minimize variations in the size and position of the focused spot.

In one embodiment, a mirror is used to reflect light from the source into the end of the waveguide. This can be used to provide a more compact optical design. The mirror can also contain set screws to provide x-y adjustment of the position of the spot from the source on the end of the waveguide. In the current configuration the mirror is permanently glued into position once the spot has been aimed. An alternative arrangement can use either a one degree of freedom or completely fixed mirror and shift the laser or lens position to aim the spot. In yet another alternative, an adjustable position mirror can be used to vary the angle of incidence.

The response of the sensor is measured through the use of a photodetector. In one embodiment, the detector can be mounted at the bottom of the waveguide at the opposite end from the source input. With this approach the amount of light coupled into the refractive medium (air, water, or gas) is determined from the amount of light transmitted through the waveguide. This approach has the advantage of being the easiest to construct as well as being inherently fail-safe. A burned out optical source, broken waveguide, or other problem results in partial or total loss of light and an immediate alarm/disable signal (such as would occur upon detection of gasoline) causing the problem to be investigated and corrected.

In an alternative configurations a mirror can be positioned at the bottom end of the waveguide, thus, reflecting the light back to the top where it is detected. This provides two passes along the waveguide length which increases sensitivity. In another embodiment, detectors can be installed outside the waveguide to measure light escaping into the medium which also has a high sensitivity resulting from a dark to light detection but will lose light if the surrounding medium is dirty. Both of these alternative approaches may include lenses to more efficiently collect the light.

The optics preferably are sealed within a device housing together with an amplifier for the photodiode. A moisture absorbent material can be included to prevent condensation on the optics. In one embodiment, the device is designed to travel freely within a vertical casing so as to float at or near the surface of any water which may be present in the sampling environment. One or more holes or projections can be provided so that the device can be guided along rails or tracks within the casing.

One or more Hall effect sensors can also be included within the housing (or casing) to determine when the device is floating. A suitable Hall effect sensor, for example, can be the Model UGN3140 sensor or similar devices available from Linear Technology Corporation (Militas, Calif.). A magnet located on the top of the device can trigger a Hall effect sensor in the top of the casing when the device has floated to its top limit. In one embodiment, a conduit encases wires running to the device carrying power, ground, laser drive, laser monitor photodiode out, sensor photodiode, signal ground, and the Hall effect sensor signals. The wires can be coiled within the casing, allowing the device to travel freely.

The device housing can further include various electronic signal processing and control elements, if desired, for example to activate and drive the laser diode, apply thresholds to the sensor's signal and/or communicate with a central monitoring system or host control system.

It is possible that very small condensation droplets or frost particles can cause false triggering of the sensor. This is believed to be due to either the diffraction or geometrical reflection of evanescent waves at the waveguide's surface. Light leaking from the waveguide in this manner is diffusely scattered, in contrast to light leaving from a gasoline layer which remains at the angle of transmission forming a cone of light which propagates downward. To address this potential problem, the device can further include a simple photodetector to prevent the frost/dew false alarms. Such a photodetector can be installed at the top of the device, facing downward toward the waveguide, and will only receive light from the frost/dew condition. Light from a layer of gasoline will propagate downward away from the detector. This additional sensor will indicate when this error condition is occurring and disable the alarm. Alternatively, a heater can be used to heat the waveguide or coating can be applied to minimize such effects.

The invention will next be described in connection with certain preferred embodiments. However, it should be made clear that various changes and modifications can be made by those skilled in the art without departing from the spirit or scope of the invention. For example, the shape of the waveguide can be varied. There are no restrictions on the shape of the cross-section. The waveguide does not need to be mounted exactly on the vertical and adjusting the angle of the waveguide relative to the liquid/air interface will adjust the sensor's sensitivity. Variants employing a curved or otherwise shaped waveguide are feasible and a flexible optical fiber (e.g., with the outer cladding stripped or using cladding propagation modes) could be used in the place of a rigid waveguide.

BRIEF DESCRIPTION OF THE DRAWINGS

FIG. 8A is a schematic illustration of an optical waveguide, such as illustrated in FIG. 7, showing an alignment of the waveguide with a light source;

FIG. 8B is an alternative illustration of the waveguide of FIG. 8A;

FIG. 9A is a schematic illustration of the operation of the present invention in air;

FIG. 9B is a schematic illustration showing the operation of the present invention in a fluid that does not degrade internal reflection within the waveguide;

FIG. 9C is a schematic illustration, showing the principle of operation in the present invention in a fluid that does degrade internal reflection within the waveguide;

DETAILED DESCRIPTION OF THE DRAWINGS

Figure 1:
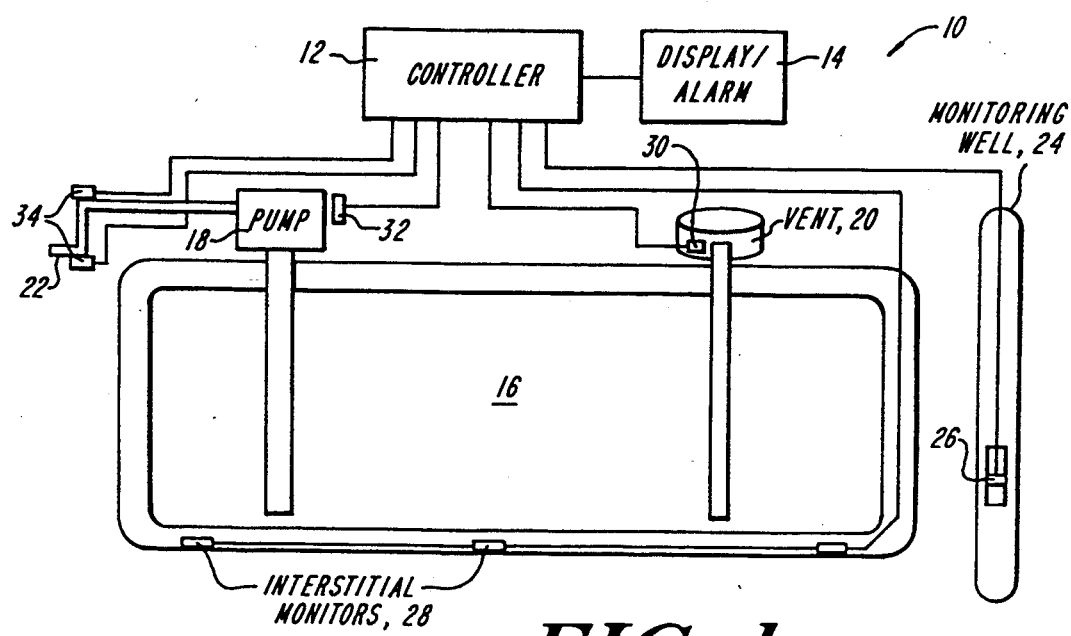
FIG. 1 is a schematic block diagram of a comprehensive hydrocarbon sensor system for use in monitoring gasoline service stations according to the invention.

In FIG. 1, a comprehensive sensor system 10 is shown, for use in monitoring hydrocarbon leaks from a gasoline service station. The system can include controller 12, display/alarm unit 14, and plurality of sensors to monitor the integrity of gasoline storage tank 16 and associated elements e.g., pump 18, vent 20, underground piping 22 and monitoring well 24. As shown in FIG. 1, the system can include bore hole sensors 26, vent sensors 30, pump sensors 32 and pipe joint sensors 34.

Figure 2:
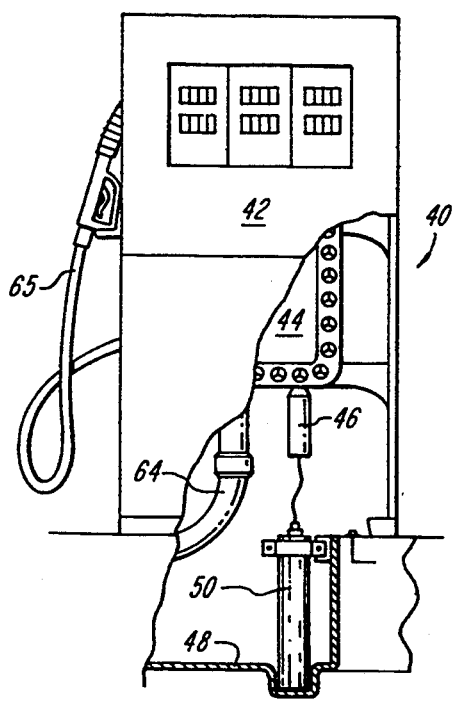
FIG. 2 is a partial, cross-sectional side view of a gasoline service station dispenser and pan, employing a sensor according to the present invention.

In FIG. 2, a partial, cross-sectional view of another sensor system 40 for use in a gasoline and service station is shown. In this embodiment, a gasoline dispenser 42 is depicted as being situated above a shallow collection pan 48. The dispenser 42 includes a conventional dispenser field wiring junction box 44 which serves to control the flow of gasoline from input pipe 64 to nozzle and hose assembly 65 housing the electronic controls associated with the gasoline dispenser. As shown in FIG. 2, a sensor 50 can be disposed within the pan 48 to detect any hydrocarbon leaks. The sensor is connected to the field wiring junction box via a controller/shut-off switch 46 which deactivates the dispenser 42 in the event that a hydrocarbon leak is detected in the dispenser pan. (Obviously, in some applications, the controller and/or shut-off switch can be physically located within the junction box 44, itself.) One suitable shut-out switch is the Model RKS-5AG-120 relay, commercially available from Pottery Brumfield Co. (Princeton, Ind.). The sensor system 40 can also be integrated into an overall monitoring system, such as the system 10 shown in FIG. 1.

Figure 3:
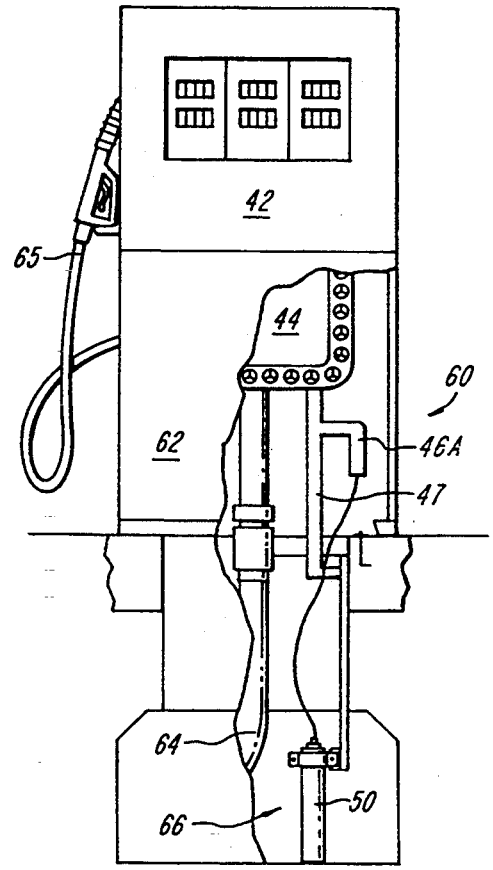
FIG. 3 is another partial cross-sectional view of a gasoline service station dispenser employing a sump-based sensor according to the invention.

In FIG. 3, another sensor system 60 according to the invention is shown for use in conjunction with a dispenser 44 having a deep sump 66. Again, field wiring junction box 44 controls the flow of gasoline from input pipe 66 to nozzle 65. In the illustration of FIG. 3, a sensor 50 is disposed at the bottom of the sump 66 and connected to a controller/shut-off switch 46A. In this embodiment, the controller/shut-off switch 46A is isolated from the main junction box but serves to shut off the main power line 47 from the gasoline service station's power supply to the dispenser 42.

Figure 4:
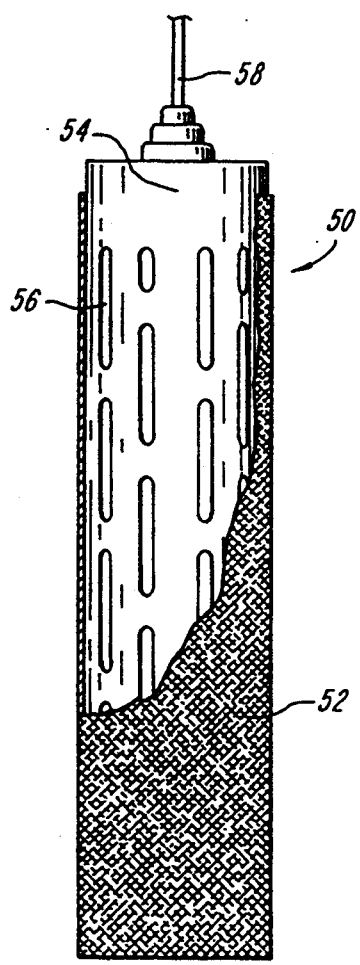
FIG. 4 is an external, partially cut-away side view of a sensor assembly according to the invention.
Figure 5:
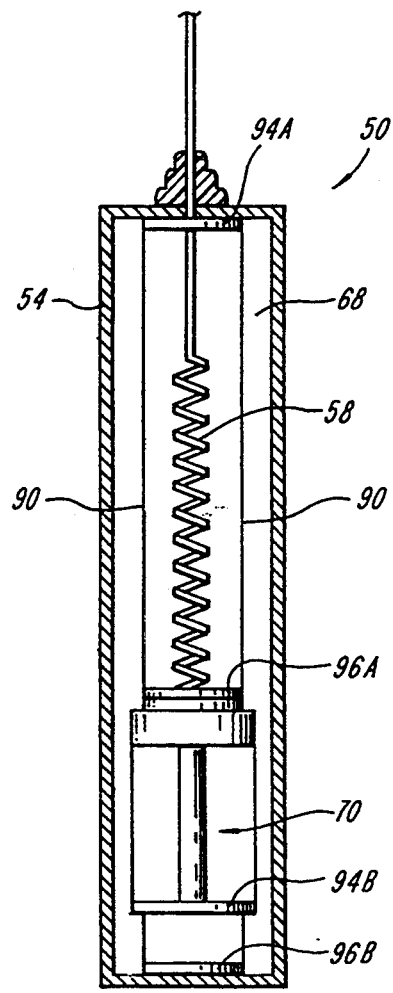
FIG. 5 is a cross-sectional view of then sensor of FIG. 4.

In FIGS. 4 and 5, a sensor assembly 50, suitable for the applications described above in connection with FIGS. 2 and 3 (as well as bore holes) is shown in more detail. FIG. 4 provides a partially cut-away, external side view of a sensor assembly, including a dust cover 52 and a casing 54 having a least one opening 56 which permits ready passage of any fluids present in the external environment into the inside of the sensor assembly. Wires 58 provide electrical connection between a buoyant detector device disposed within the assembly and a remote controller or display unit.

In FIG. 5, a cross-sectional view of the sensor 50 is shown, including the casing 54 and a detector device 70 which is free to ride up and down on rails 90, thus, permitting the detector device 70 to float at a buoyed level anywhere within the housing 54, in the event that water and/or other fluids fill the inner chamber 68 of the casing 54. The portion of electrical cable 58 that is disposed within the sensor body can be coiled, as shown, to permit movement of the detector device 70 up and down without tangling.

Also shown in FIG. 5 are Hall sensors 94A and 94B which serve to determine when the sensing device 70 is situated either at top of the sensor housing (in which case a signal will be sensed by sensor 94A) or at the bottom of the housing (where sensor 94B would be activated). The two Hall effect sensors are disposed, such that the presence of magnetic plates 96A and 96B will activate the sensors, thereby indicating a top-of-column or bottom-of-column situation.

Figure 6:
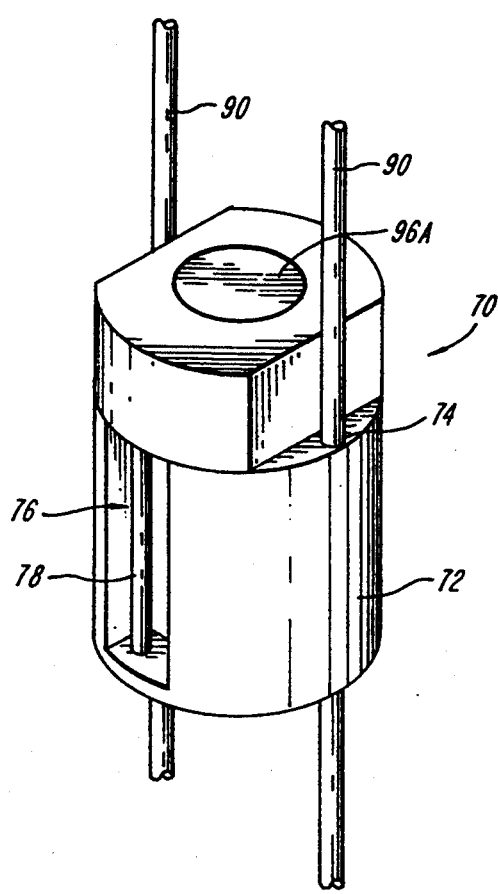
FIG. 6 is a schematic illustration of the measuring apparatus employed in the sensor of FIGS. 4 and 5.

FIG. 6 provides a more detailed schematic view of a detector device 70 according to the invention. As shown, the device 70 includes a housing 72 having guide channel holes 74 through which guide rails 90 pass. The housing 70 also includes a sampling bay 76 in which an optical waveguide 78 is disposed. As described above, the sensing device can further include one or more Hall effect sensor for determining the location of the detector within a columnar casing. In the illustrated embodiment, a magnetic plate 96A is shown at the top of the device housing to serve as a trigger for a Hall effect sensor disposed above it in the casing (as shown in FIG. 5).

Figure 7:
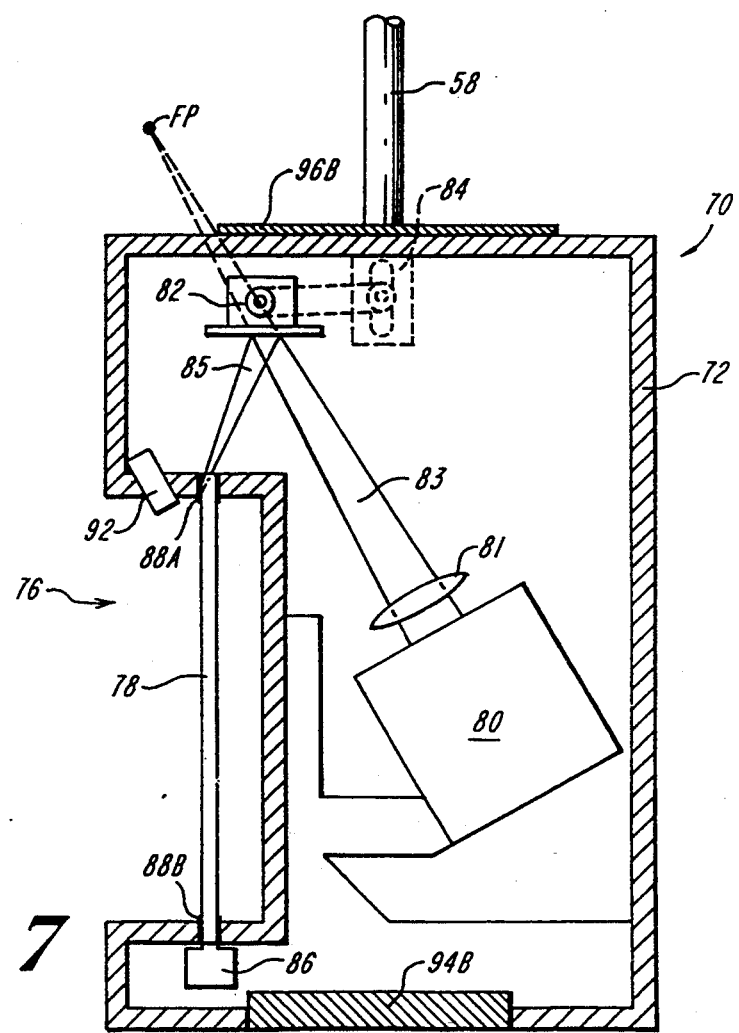
FIG. 7 is a cross-sectional view of the device of FIG. 6.

FIG. 7 shows a cross-sectional view of the device 70, including housing 72, sampling bay 76 and optical waveguide 78. Also disposed within the housing is a light source 80 (e.g., a laser of light emitting diode) and, optionally, a mirror 82 which reflects the light beam 83 emitted by the light source 80, such that it is incident on a face of the waveguide 78. As shown, a focusing lens 81 can be used to focus the light to a theoretical focal point (FP). Because of the location of mirror 82, the light beam is folded, such that a reflected beam 85 is focused to a point FP within the waveguide.

By varying the angle of incidence, as discussed in more detailed below, the present invention can be used to detect fluids present in the ambient environment and even selectively discriminate between fluids based upon their attenuation of light traveling through the waveguide after such light enters at a predetermined angle. The angle of incidence can be determined by fixing mirror 82 in a particular position or, alternatively, by varying the location of the mirror. For adjusting the angle of incidence, an actuator 84 can be optionally employed, as shown, or other translating, rotating, or oscillating means can be used to alter the orientation of mirror 82.

FIG. 7 also illustrates further the use of Hall sensors to determine the vertical location of the device 70. As illustrated, a Hall sensor 94B is situated at the bottom of the device housing 72. When this Hall effect sensor is in contact with, or close proximity, a magnetic plate disposed in the bottom of the sensor assembly (as illustrated schematically in FIG. 5), a signal will be generated. As similar Hall effect sensor can be located at the top of the sensor assembly (again, as illustrated in FIG. 5) to interact with the magnetic plate 96B at the top of device casing 72, as shown. (Obviously, other arrangements of the Hall effect sensors can be employed and other electrical or mechanical sensors can be substituted for the Hall effect sensors. The illustrated embodiment requires only one Hall effect sensor to be located within the device 70, itself, thereby minimizing the number of wires that must be bundled together within conduit 58.

In operation, light from laser 80 will travel through waveguide 78 by internal reflection until the light is detected at the bottom of the waveguide by detector 86, unless the fluid-to-be-tested is present in the sample bay 76 and contacts the sides of the waveguide 78 to cause attenuation. (In order to minimize non-specific light losses, the ends of the waveguide can be coated with a reflective material, such as silver or another highly reflective metal coating, as illustrated by coating 88A and 88B in those places where the waveguide passes through or comes in close proximity with the device casing.)

Additionally, the device of FIG. 7 can include a second detector element 92 disposed outside of the waveguide to detect light which is scattered or otherwise loss at the boundary between the waveguide and the ambient environment of the sample bay 76. Sensor 92 is particularly useful in detecting non-specific signal attenuations which may be due to frost or condensation on the surface of the waveguide.

FIG. 8A illustrates the principles of operation in the present invention in more detail. The incident light beam 85 is directed to the surface 78 of waveguide 78 at an angle φ. Upon entering the waveguide, the light beam typically will be bent slightly while continuing to undergo focusing. The focal point FP' may occur shortly after the entry of the beam 85 into the waveguide 78 or after one or more internal reflections. Alternatively, as shown in FIG. 8B, the focal point FP" can occur before the beam enters the rod thereby permitting the beam to spread and illuminate a major portion of the end face upon incidence. In either event, the light beam will continue to travel down the waveguide following a zig-zag path centered about the beam axis 89.

As explained in more detail below, the angle of incidence φ (or its rough complement θ) is critical to distinguishing fluids that may be in contact with the waveguide sidewalls 91.

For example, as illustrated in FIG. 9A, a light beam 85 entering waveguide 78 at most angles will be internally reflected, as shown, in the presence of air 100 in the ambient environment. Moreover, as illustrated in FIG. 9B, an angle of incidence can be chosen, such that the laser beam 85 entering waveguide 78 will be reflected not only in air 100 but also if water 102 is present in the ambient environment of the sampling bay. However, as illustrated in FIG. 9C, if a hydrocarbon material or other fluid having a higher index of refraction 104 is also present in the ambient environment, the interface dynamics of the waveguide where it is in contact with the fluid layer 104 will result in a loss of internal reflectivity, and thereby allow the transmission of light out of the waveguide. Based on this principle, hydrocarbons (or any other fluids for which detection is sought) can be selectively identified using one or more discriminating sensors having light sources incident at predetermined angles.

Figure 10:
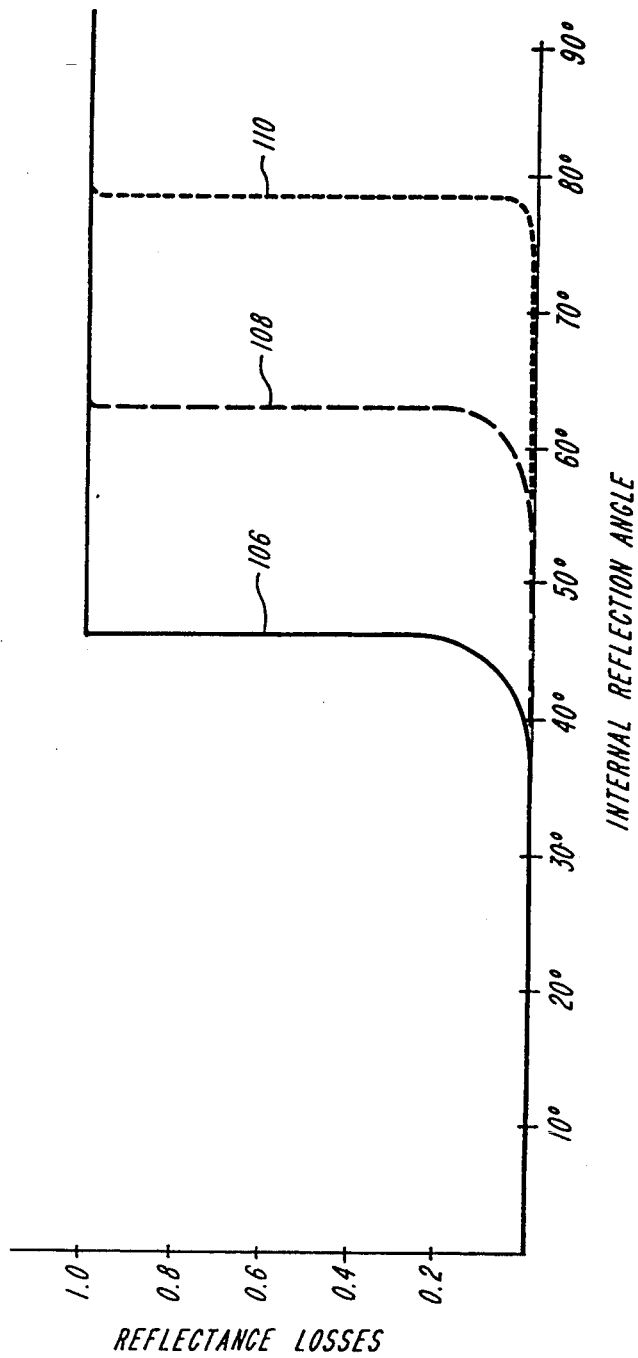
FIG. 10 is a graph illustrating the transmission coefficience for a waveguide in various ambient environments.

The principles of operation are further illustrated in FIG. 10 which is a graph of reflectance losses versus internal reflectance angle φ for three distinct waveguide interfaces. Curve 106 (illustrated by the solid line) shows the reflectivity changes for an interface between a glass waveguide (having a nominal index of refraction of about 1.454) and an ambient environment of air (having an index of refraction equaling 1.0). The graph shows that an internal reflectance angle of approximately less than 45° is necessary before there are significant reflectivity losses in air.

Curve 108 (illustrated by the dashed lines) shows the reflectance losses associated with varying angles at an interface between an optical fiber (again, having a nominal index of refraction of approximately 1.454) and water (having an index of refraction of about of 1.33). In this instance, the internal reflectance angle must be less than about 60° before there is a significant loss in reflectance in water.

Finally, curve 110 (illustrated by the dotted line) depicts the reflectance losses at various angles for an interface between a glass waveguide (n=1.454) and a hydrocarbon sample having an index refraction of about 1.43. Thus, curve 110 shows that the internal reflectance angle must be less than about 80° for there to be significant reflectance losses in the presence of gasoline.

Based on the foregoing, it should be clear that the angle of incidence illustrated in FIG. 8 can be selected to discriminate gasoline (or other hydrocarbons) from air or water which may also be present in the sampling environment. For a optical waveguide of about 1 millimeter in width or diameter and a light source in the red or infrared region, an optimal angle of incidence is approximately 29°. More generally, to detect the presence of gasoline (or other hydrocarbons) with detectors in accordance with the present invention, the angle of incidence is preferably selected to be between about 34° and about 25°, more preferably between 31° and 27°. While angles below 24° can also be used in the detection of hydrocarbons, it has been found that the signal (the degree of attenuation) is much weaker and harder to quantify.

Figure 11:
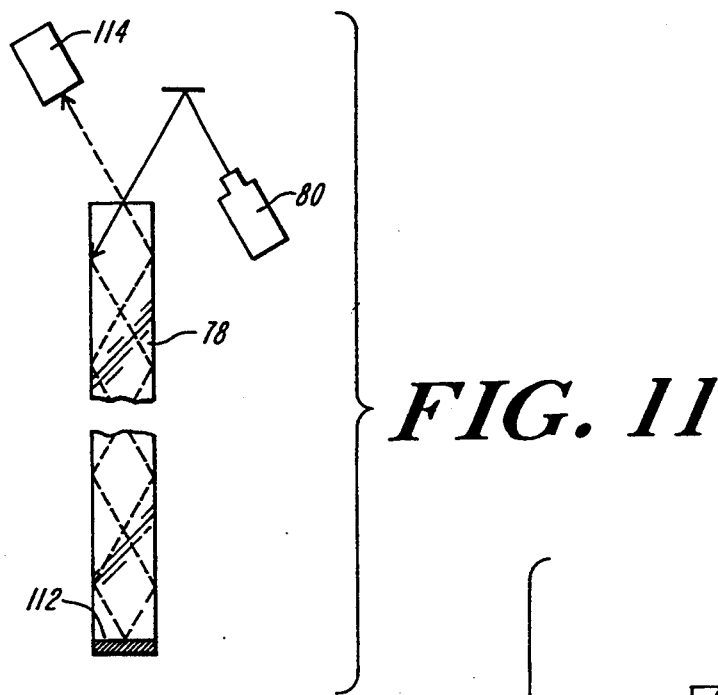
FIG. 11 is a schematic illustration of an embodiment in the present invention employing a reflective surface at the end of the waveguide.

In FIG. 11, an alternative embodiment of the invention is shown in which light from source 80 is transmitted into a waveguide 78 and allowed to travel to the bottom of the waveguide where it is reflected by mirrored surface 112. The light returns via another internal reflectance path until it exits the same face of the waveguide as it originally enters and is detected there by detector 114.

Figure 12:
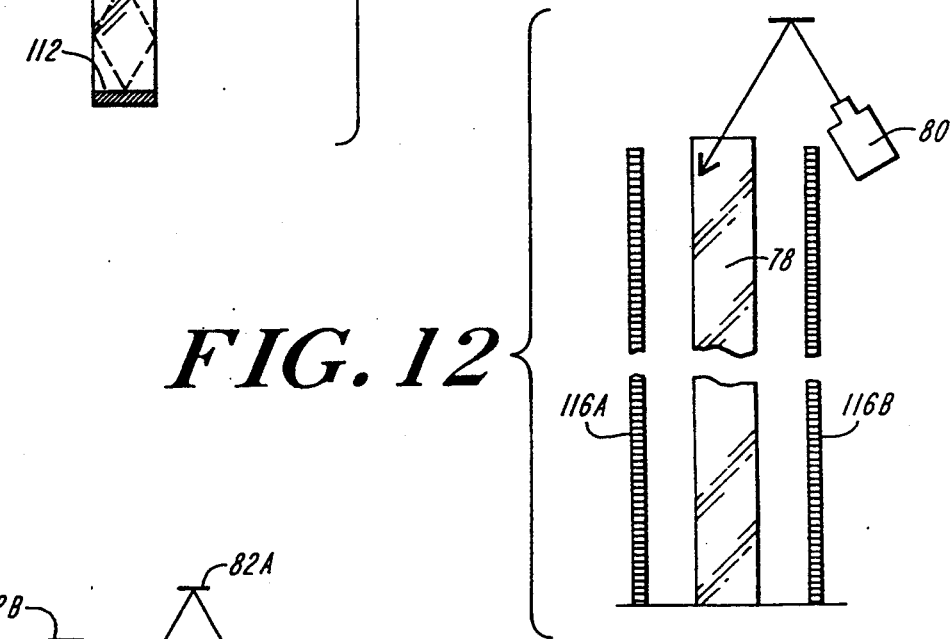
FIG. 12 is an illustration of another embodiment of the invention employing externally disposed detector elements.

In FIG. 12, another embodiment of the invention is illustrated in which the light from laser 80 is again directed into the waveguide 78, but the detector at the other end of the waveguide is replaced by one or more arrays of external detectors 116A and 116B which detect the light which escapes from the waveguide.

Figure 13:
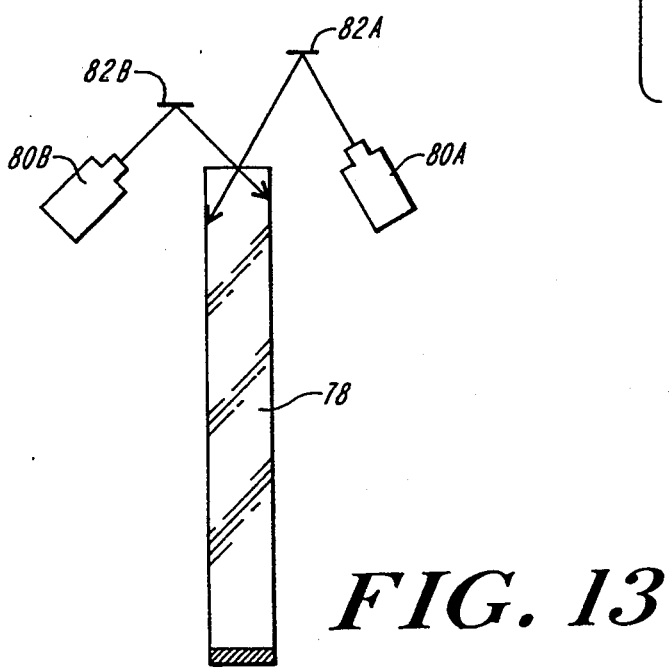
FIG. 13 is yet another embodiment of the invention employing two light sources.

FIG. 13 illustrates yet another embodiment of the invention in which two laser sources 80A and 80B are employed to introduce light into the waveguide 78 at different angles of incidence (via mirrors 82A and 82B). Such an embodiment is particularly useful in detecting both water and gasoline (or any two dissimilar liquids).

Figure 14:
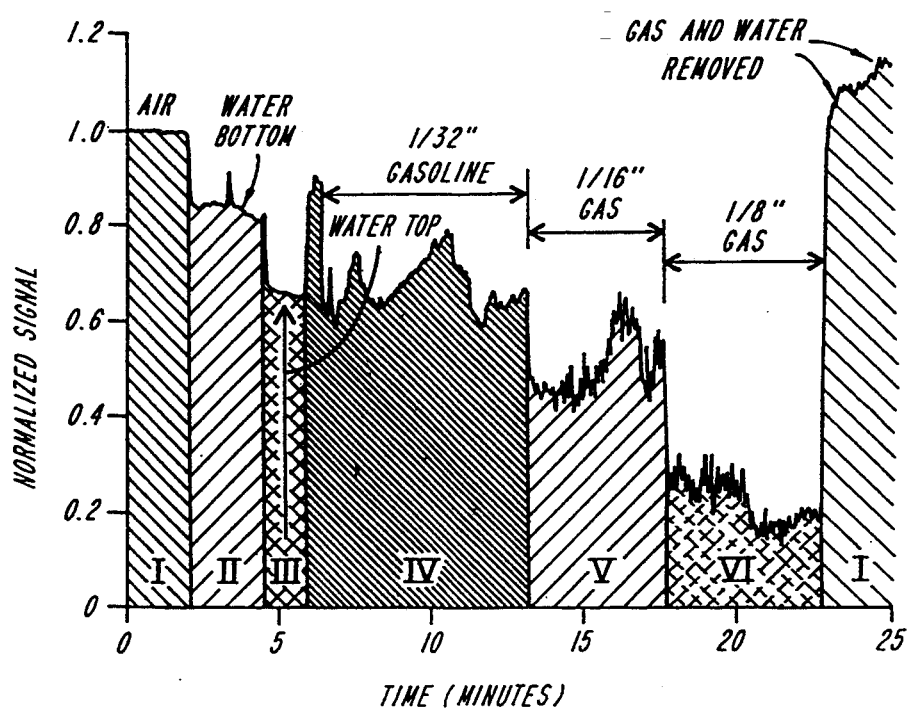
FIG. 14 is a graph of experimental data illustrating the operation of a sensor according to the invention in various ambient environments.

FIG. 14 shows experimental data obtained with a device similar to the device illustrated in FIGS. 4–7. In the experimental embodiment, a laser diode (Model LTO22MC, Sharp, Osaka, Japan) emitting light at about 780 manometers, was employed together with a fused silica optical waveguide of cylindrical shape, about 1 millimeter in diameter and about 4 centimeters in length. The detector was a silicon photodetector (Model 1787-08, Hamamatsu Photonics, Hamamatsu City, Japan). The laser was operated at about 3 milliwatts and emitted light in a continuous wave (CW) mode. (In some applications, it may be preferable to operate the light source in a pulsed mode, for example, emitting a pulse of light of 50–200 milliseconds duration every 2 to 5 seconds.)

The protocol of the experiments illustrated in FIG. 14 called for initial measurements to be taken in an air environment (Region I). A second set of measurements were taken after water was added to the bottom of the sampling well in which the sensing device was situated (Region II). Water continued to be added until the device was totally immersed (Region III). Some of the water was then removed, and a very thin layer of gasoline added. This gasoline formed a sheen on the top of the water (Region IV). Gasoline continued to be added until 1/16 inch of gasoline was present in the sampling bay (Region V). Gasoline continued to be added until an ⅛ inch of gasoline was present in contact with the waveguide (Region VI). Finally, the water and gasoline was removed and the device returned to the original conditions of ambient air (Region I).

I claim:

1. A sensor for detecting a fluid in an ambient environment, the sensor comprising:
   a sample chamber:
   an optical waveguide having a central axis along which light can transmitted the waveguide being disposed in said sample chamber, such that a fluid present in the chamber contacts at least a portion of the waveguide;

a floatation means for floating the waveguide on a liquid present in the environment;

irradiation means for projecting light into a first end of said waveguide, detector means for detecting the amount of light propagated through the waveguide, and characterized in that the irradiation means is aligned with the waveguide, such that the light incident on the waveguide enters said first end at an angle relative to the central axis and propagates by internal reflection within the waveguide rather than direct transmittance, such that optimal propagation occurs in the absence of said fluid, and the presence of a fluid in contact with the waveguide causes detectable losses in light propagation due to degradation of said internal reflectance.

2. The sensor of claim 1 wherein the detector means is a silicon photodetector.

3. The sensor of claim 1 wherein the floatation means is a buoyant housing surrounding said waveguide, irradiation means and detector means.

4. The sensor of claim 1 wherein the floatation means further comprises guide means for guiding floatational movement of the sensor in a vertical direction.

5. The sensor of claim 1 wherein the sensor further comprises a position sensing means for determining the location of the sensor.

6. The sensor of claim 5 wherein the position sensing means comprises a Hall effect sensor for determining when the sensor is at a top position within a casing.

7. The sensor of claim 5 wherein the position sensing means comprises a Hall effect sensor for determining when the sensor is at a bottom position within a casing.

8. The sensor of claim 1 wherein the optical waveguide is fused silica.

9. The sensor of claim 1 wherein the optical waveguide is a cylindrical rod.

10. The sensor of claim 1 wherein the sensor is capable of measuring water and the angle of incidence ranges from about 38° to about 75°.

11. The sensor of claim 1 wherein the sensor is capable of measuring hydrocarbons and the angle of incidence ranges from about 24° to about 34°.

12. The sensor of claim 1 wherein the sensor further comprises means for adjusting the angle of incidence.

13. The sensor of claim 1 wherein the sensor further at least two irradiation means aligned with the waveguide to project light at least two different angles of incidence.

14. The sensor of claim 1 wherein the irradiation means is a light-emitting diode.

15. The sensor of claim 1 wherein the irradiation means is a laser.

16. A fuel leak sensor, comprising:

an elongate glass rod forming an optical axis between a distal end and a proximal end, said optical axis being substantially concentric to the cross-sectional area of said rod, said proximal end having a planar face that is substantially perpendicular to said optical axis:

a laser for generating a laser beam at a wavelength suitable for transmission in said rod, said laser beam coupled to said glass rod and incident at said proximal end for transmission into said rod, said laser beam aligned to form a preselected angle between 24 and 34 degrees relative to said optical axis, said angle and said wavelength chosen such that said laser beam effects total internal reflection within said rod where said rod contacts water or air, and such that said laser beam is transmitted out of said rod where said rod contact fuel:

a detector optically coupled to said distal end of said rod, and responsive to said laser beam wavelength, said detector arrayed to collect substantially all of the energy of said laser beam transmitted and reflected within said rod; and detector processing electronics in communication with said detector, said electronics providing an indication that the energy collected by said detector is less than a preselected level, said level corresponding to the loss in energy which occurs when said laser beam is transmitted out of said rod due to the presence of fuel in contact with said rod.

17. The sensor of claim 16 wherein said laser generates a laser beam of approximately 780 nm and operates at approximately 3 mW of power.

18. The sensor of claim 16 wherein said laser is pulsed between approximately 50 and 100 Hz at intervals between approximately 0.2 and 0.5 Hz.

19. A sensor for detecting a fluid in an ambient environment, the sensor comprising:

a sample chamber;

an optical waveguide having a central axis along which light can transmitted, the waveguide being disposed in said sample chamber, such that a fluid present in the chamber contacts at least a portion of the waveguide;

irradiation means for projecting light into a first end of said waveguide; and detector means tier detecting the amount of light propagated through the waveguide; and a scattered light detecting means tier detecting light scattered by moisture on the waveguide, characterized in that the irradiation means is aligned with the waveguide, such that the light incident on the waveguide enters said first end at an angle relative to the central axis, and propagates by internal reflection within the waveguide rather than direct transmittance, such that optimal propagation occurs in the absence of said fluid, and the presence of a fluid in contact with the waveguide causes detectable losses in light propagation due to degradation of said internal reflectance.

20. A liquid detection sensor, comprising:

an elongate optical waveguide forming an optical axis between a distal end and a proximal end, said optical axis being substantially concentric to the cross-sectional area of said optical waveguide, said cross-sectional area selected such that energy beam successively reflects within said optical waveguide at a frequency representative of the minimum layer thickness of said liquid to be detected by said sensor, said proximal end having a planar face that is substantially perpendicular to said optical axis;

an energy source for generating an energy beam at wavelengths suitable for transmission within said optical waveguide, said energy beam coupled to said optical waveguide and incident at said proximal end for transmission into said optical waveguide, said energy beam aligned to form a preselected angle relative to said optical axis, said angle and said wavelengths chosen such that said energy beam effect total internal reflection within said optical waveguide where said optical waveguide contacts air, and such that said energy beam is transmitted out of said optical waveguide where said optical waveguide contacts said liquid:
a detector responsive to said wavelengths and optically coupled to said distal end, said detector arranged to collect substantially all of said energy beam transmitted and reflected within said optical waveguide; and
detector processing electronics in electrical communication with said detector, said electronics providing an indication that the energy by said detector is less than a preselected level, said level corresponding to the loss in energy which occurs when said energy beam is transmitted out of said optical waveguide due to the presence of said liquid in contact with said optical waveguide.

21. The sensor of claim 20 wherein said optical waveguide is formed by fused silicon.

22. The sensor of claim 20 wherein said preselected angle is between about 24 and 34 degrees and wherein said liquid is gasoline.

23. The sensor of claim 20 wherein said preselected angle is between about 38 and 75 degrees and wherein said liquid is water.

24. The sensor of claim 20 further comprising collection optics, said optics optically coupled between said optical waveguide and said detector to improve the collection efficiency of energy transmitted through and reflected within said optical waveguide.

25. The sensor of claim 20 wherein the active element of said detector is silicon.

26. The sensor of claim 20 wherein said detector is mounted directly at the distal end of said optical waveguide.

27. The sensor of claim 20 wherein said optical waveguide is constructed with material having an index of refraction that is substantially similar to the index of refraction of said liquid.

28. The sensor of claim 20 when said optical waveguide forms a cylindrical glass rod.

29. The sensor of claim 28 wherein said cylindrical glass rod is approximately 1 mm in diameter.

30. The sensor of claim 28 wherein said optical waveguide is a flexible optical fiber.

31. A sensor for detecting a fluid in an ambient environment, the sensor comprising:
a sample chamber;
an optical waveguide having a central axis along which light can transmitted, the waveguide being disposed in said sample chamber, such that a fluid present in the chamber contacts at least a portion of the waveguide, and wherein the waveguide is mirror coated in regions where the waveguide is secured to a housing;
irradiation means tier projecting light into a first end of said waveguide;
detector means for detecting the amount of light propagated through the waveguide; and
characterized in that the irradiation means is aligned with the waveguide;
such that the light incident on the waveguide enters said first end at an angle relative to the central axis, and propagates by internal reflection within the waveguide rather than direct transmittance, such that optimal propagation occurs in the absence of said fluid, and the presence of a fluid in contact with the waveguide causes detectable losses in light propagation due to degradation of said internal reflectance.

32. A liquid detection sensor, comprising:
an elongate optical waveguide forming an optical axis between a distal .encl and a proximal end, said optical axis being substantially concentric to the cross-sectional area of said optical waveguide, said proximal end having a planar face that is substantially perpendicular to said optical axis;
a sensor housing for supporting said optical waveguide, said optical waveguide mirrored at points in contact with said housing and with adhesives utilized to attach said optical waveguide to said housing;
an energy source for generating an energy beam at wavelengths suitable for transmission within said optical waveguide, said energy beam coupled to said optical waveguide and incident at said proximal end for transmission into said optical waveguide, said energy beam aligned to form a preselected angle relative to said optical axis, said angle and said wavelengths chosen such that said energy beam effect total internal reflection within said optical waveguide where said optical waveguide contacts air, and such that said energy beam is transmitted out of said optical waveguide where said optical waveguide contacts said liquid:
a detector responsive to said wavelengths and optically coupled to said distal end, said detector arranged to collect substantially all of said energy beam transmitted and reflected within said optical waveguide: and
detector processing electronics in electrical communication with said detector, said electronics providing an indication that the energy by said detector is less than a preselected level, said level corresponding to the loss in energy which occurs when said energy beam is transmitted out of said optical waveguide due to the presence of said liquid in contact with said optical waveguide.

33. A liquid detection sensor, comprising:
an elongate optical waveguide forming an optical axis between a distal end and a proximal end, said optical axis being substantially concentric to the cross-sectional area of said optical waveguide, said proximal end having a planar face that is substantially perpendicular to said optical axis;
an energy source for generating an energy beam at wavelengths suitable for transmission within said optical waveguide, said energy beam coupled to said optical waveguide and incident at said proximal end for transmission into said optical waveguide, said energy beam aligned to form a preselected angle relative to said optical axis, said angle and said wavelengths chosen such that said energy beam effect total internal reflection within said optical waveguide where said optical waveguide contacts air, and such that said energy beam is transmitted out of said optical waveguide where said optical waveguide contacts said liquid;
a detector responsive to said wavelengths and optically coupled to said distal end, said detector arranged to collect substantially all of said energy beam transmitted and reflected within said optical waveguide;
detector processing electronics in electrical communication with said detector, said electronics providing an indication that the energy by said detector is less than a preselected level, said level corresponding to the loss in energy which occurs when said energy beam is transmitted out of said optical waveguide due to the presence of said liquid in contact with said optical waveguide;

a scatter detector, in communication with said detector electronics, said scatter detector optically coupled near to the outer surface of said optical waveguide and responsive to scattered energy from said optical waveguide due to dew or frosting conditions.

34. The sensor of claim 33 wherein said detector electronics disenables said indicator when said scatter detector measures scattered energy which exceeds a preselected level.

35. A liquid detection sensor, comprising:

an elongate optical waveguide forming an optical axis between a distal end and a proximal end, said optical axis being substantially concentric to the cross-sectional area of said optical waveguide, said proximal end having a planar face that is substantially perpendicular to said optical axis.

said distal end having a mirrored surface to reflect the energy transmitted and reflected within said optical waveguide;

a floatation means for floating the waveguide on a liquid present in the environment, a sample chamber:

an energy source for generating an energy beam at wavelengths suitable for transmission within said optical waveguide, said energy beam coupled to said optical waveguide and incident at said proximal end for transmission into said optical waveguide, said energy beam aligned to form a preselected angle relative to said optical axis, said angle and said wavelengths chosen such that said energy beam effects total internal reflection within said optical waveguide where said optical waveguide contacts air, and such that said energy beam is transmitted out of said optical waveguide where said optical waveguide contacts said liquid;

a detector responsive to said wavelengths and optically coupled to said proximal end, said detector arranged to collect substantially all of said energy beam transmitted and reflected within said optical waveguide; and detector processing electronics in electrical communication with said detector, said electronics providing an indication that the energy collected by said detector is less than a preselected level, said level corresponding to the loss in energy which occurs when said energy beam is transmitted out of said optical waveguide due to the presence of said liquid in contact with said optical waveguide.

36. A liquid detection sensor, comprising:

an elongate optical waveguide forming an optical axis between a distal end and a proximal end, said optical axis being substantially concentric to the cross-sectional area of said optical waveguide, said proximal end having a planar face that is substantially perpendicular to said optical axis;

an energy source for generating an energy beam at wavelengths suitable for transmission within said optical waveguide, said energy beam coupled to said optical waveguide and incident at said proximal end for transmission into said optical waveguide, said energy beam aligned to form a preselected angle relative to said optical axis, said angle and said wavelengths chosen such that said energy beam effects total internal reflection within said optical waveguide where said optical waveguide contacts air, and such that said energy beam is transmitted out of said optical waveguide where said optical waveguide contacts said liquid:

at least one array of external detectors which detect energy transmitted out of said optical waveguide where said optical waveguide contacts liquid; and detector processing electronics in communication with said detector, said electronics providing an indication that the energy collected by said detector exceeds a preselected level, said level corresponding to the amount of energy which escapes from said optical waveguide when said energy beam is transmitted out of said optical waveguide due to the presence of said liquid in contact with said optical waveguide.

* * * * *